United States Patent [19]

Christinger

[11] Patent Number: 4,543,093
[45] Date of Patent: Sep. 24, 1985

[54] VARIABLE SEALING PRESSURE PLUNGER ROD ASSEMBLY

[75] Inventor: Werner Christinger, Franklin Lakes, N.J.

[73] Assignee: Becton, Dickinson and Company, Paramus, N.J.

[21] Appl. No.: 677,124

[22] Filed: Dec. 3, 1984

Related U.S. Application Data

[63] Continuation-in-part of Ser. No. 451,307, Dec. 20, 1982, Pat. No. 4,500,310.

[51] Int. Cl.⁴ .............................................. A61M 5/00
[52] U.S. Cl. .................................................. 604/228
[58] Field of Search ......................... 604/218, 228, 230

[56] References Cited

U.S. PATENT DOCUMENTS

| 422,437 | 3/1890 | Otto | 604/230 X |
|---|---|---|---|
| 2,895,773 | 7/1959 | McConnaughey | 604/230 X |
| 3,628,523 | 12/1971 | Pirtle, Jr. | 604/230 |
| 3,635,218 | 1/1972 | Ericson | 604/230 X |
| 3,828,778 | 8/1974 | Weinhart | 604/228 |
| 4,074,715 | 2/1978 | Geiger | 604/230 |
| 4,180,069 | 12/1979 | Walters | 604/228 |
| 4,500,310 | 2/1985 | Christinger | 604/228 |

FOREIGN PATENT DOCUMENTS 78213  5/1962  France ................................ 604/228

Primary Examiner—John D. Yasko
Attorney, Agent, or Firm—John L. Voellmicke

[57] ABSTRACT

A plunger rod assembly for use with a syringe barrel comprises a plunger rod and a flexible thermoplastic stopper. A plunger rod includes an elongate shaft portion defining a longitudinal axis and having a tapered tip portion at the distal end thereof. The tapered tip portion includes a front portion at the distal end thereof and a circular tapered plunger rod wall connected to the front portion and having a convexly shaped surface. A flexible cup-shaped thermoplastic stopper includes an annular side wall and a continuous front wall connected to the side wall. An exterior surface of the side wall is larger in diameter than the syringe barrel inside diameter. The stopper interior includes an inside surface of the front wall and a tapered annular inside wall connected to the annular side wall and to the inside surface. The tapered annular inside wall and the inside surface define a cavity which has the tapered tip portion received therein. The tapered annular inside wall is inclined in the same direction as the tapered plunger rod wall and adjacent thereto. Cooperating structure for maintaining the positional relationship of the stopper and the plunger rod is also provided.

22 Claims, 25 Drawing Figures

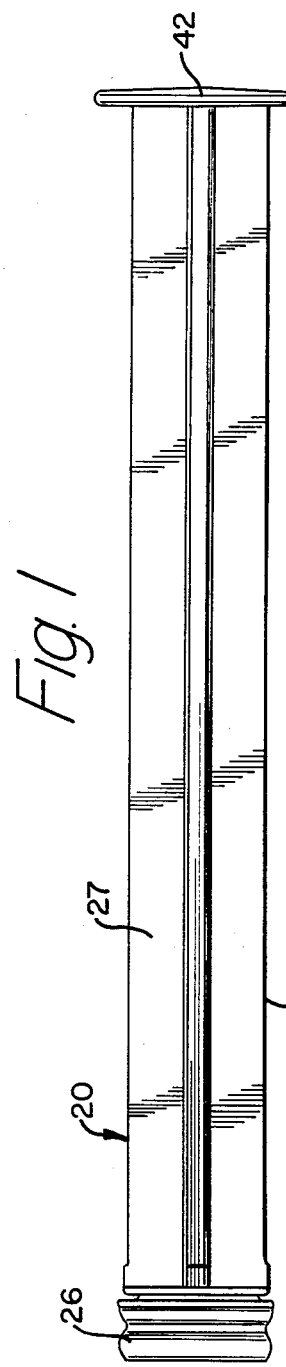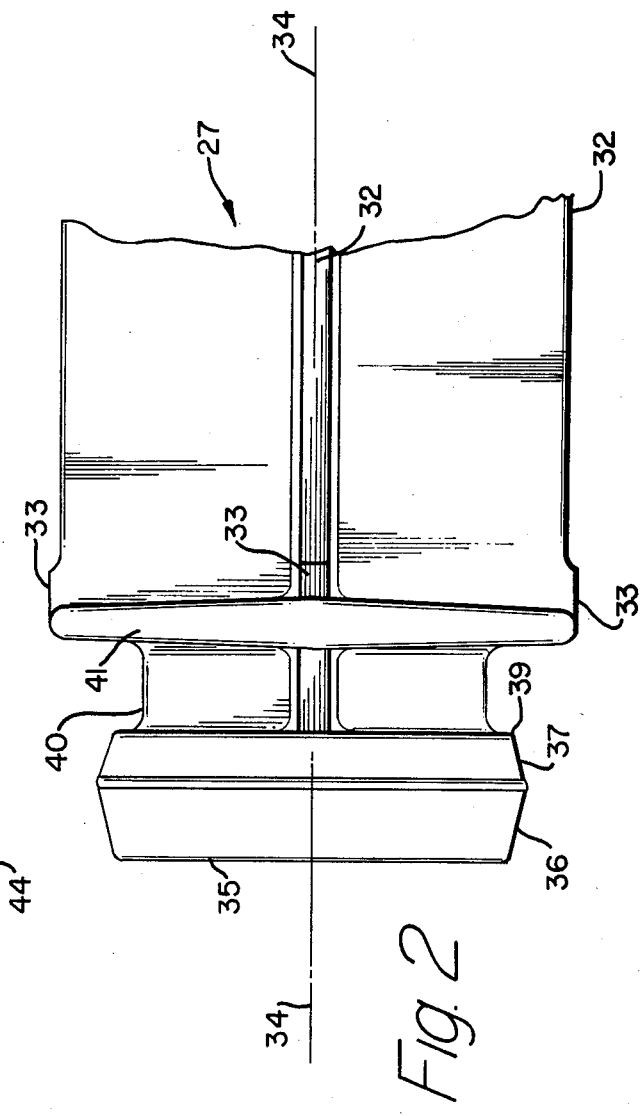

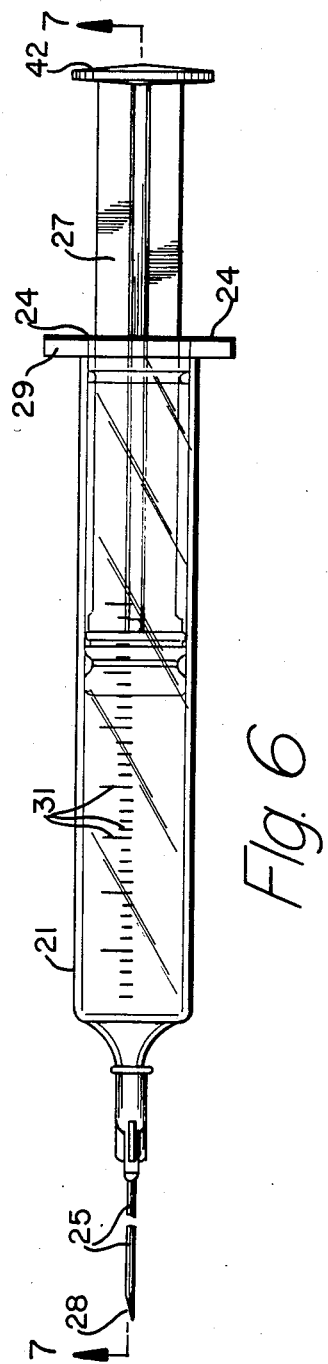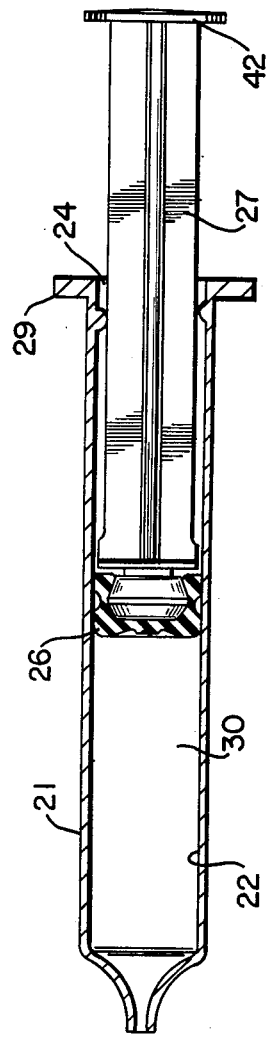
Fig. 6
Fig. 7

VARIABLE SEALING PRESSURE PLUNGER ROD ASSEMBLY

FIELD OF THE INVENTION

This application is a continuation-in-part of U.S. Application Ser. No. 451,307 filed Dec. 20, 1982 now U.S. Pat. No. 4,500,310, which is incorporated by reference herein in its entirety. The present invention relates to an apparatus and method for moving fluid along a conduit, and more particularly concerns a variable sealing pressure plunger rod assembly for use in a syringe and its method of use.

DESCRIPTION OF THE PRIOR ART

Generally speaking, a hypodermic syringe consists of a cylindrical barrel, most commonly made of thermoplastic material such as polypropylene, with a distal end adapted to be connected to a hypodermic needle and a proximal end adapted to receive a stopper and plunger rod assembly. One of the purposes of the stopper is to provide a relatively air tight seal between itself and the syringe barrel so that movement of the stopper up and down the barrel will cause liquid medication, blood or other fluids to be drawn into or forced out of the syringe through the distal end. The stopper is moved along the syringe barrel by applying axial force to the rigid plunger rod which is connected to the stopper and is sufficiently long as to be accessible outside of the barrel. The stopper should be sufficiently flexible so that it will seal the inside diameter of the barrel without requiring excessive force to move it up and down the barrel.

In order to assure an air tight seal between the syringe barrel and the stopper, known prior art stoppers are manufactured with a larger outside diameter than the inside diameter of the syringe barrels they will be used in. The syringe-stopper combination is designed so that the stopper, when introduced into the syringe barrel, is compressed enough to provide adequate pressure between the syringe and the stopper to seal this interface. As a result of this configuration, the interface of the stopper and the syringe barrel maintains, at all times, a sealing pressure capable of withstanding the challenges of filling and injecting even though this magnitude of sealing pressure is not required when the syringe is not in use.

The stopper is chemically stable so that undesirable amounts of the various chemical components of the stopper do not enter the liquid contained in the syringe. Since hypodermic syringes are frequently used to inject medication into a human body or to withdraw blood for subsequent analysis it is not desirable to have stoppers introduce foreign substances which can adversely affect the patient or the blood analysis. Hypodermic syringe stoppers are most commonly made of materials such as natural rubber or butyl rubber. Although the rubber stoppers have desirable physical properties they possess a number of disadvantages. For example, rubber stoppers contain additional chemical components such as fillers and vulcanizing accelerators which can exude to the surface and contact the liquid in the syringe wherein blood test results or medication efficacy may be affected. The problem is further aggravated when there is long term storage of liquid medication in the hypodermic syringe. Also, rubber stoppers are expensive to manufacture due to the long mold cycle time required by the vulcanization step which takes place while the stoppers are in the mold.

Recognizing the above-mentioned deficiencies in rubber stoppers, it is desirable to provide a syringe stopper made of a thermoplastic material. Normally, thermoplastic stoppers are less expensive to manufacture due to shorter molding cycle times which result in improved productivity of the molding machinery. The undesirable effects of fillers and vulcanizing agents on the liquid contents of the syringe would be eliminated since these rubber additives are not necessary in the production of thermoplastic stoppers. Also, the complexity of drug compatibility testing may be greatly reduced when thermoplastic syringe stoppers are used since both the barrel and the stopper may be constructed of materials that have similar chemical properties. In addition, the thermoplastic stopper may provide improved stability and increased shelf life for liquid medications stored in the syringe.

A major disadvantage of using a thermoplastic stopper is that over a period of time the stopper can achieve a compression set. That is, the stresses of the interference fit between the stopper and the syringe barrel can cause cold flow of the thermoplastic stopper material and thus the outside diameter of the stopper can become reduced and the stopper may no longer effectively seal the contents of the syringe.

With the above-mentioned deficiencies in mind, it is desired to provide a hypodermic syringe plunger rod assembly which is designed so that a thermoplastic stopper may be used and wherein the stopper will not be adversely affected by compression set after assembly in the syringe barrel. It is further desired to provide a thermoplastic syringe stopper which can provide increased chemical stability in order to improve long term storage capabilities, reduce interaction with liquids in the syringe and reduce the complexity of drug compatibility testing. It is also desired to provide a syringe stopper that can be manufactured with reduced cycle times on conventional injection molding equipment.

SUMMARY OF THE INVENTION

The plunger rod assembly of the present invention is useful for drawing fluids into or pushing fluids out of a receptacle having a substantially cylindrical inside wall and provided with means for receiving the plunger rod assembly and means for fluid communication with the exterior of the receptacle. This plunger rod assembly comprises a plunger rod and a flexible stopper. A plunger rod includes a rigid elongate shaft portion defining a longitudinal axis and having a tapered tip portion at the distal end thereof. This tapered tip portion includes a front portion at the distal end of the tip portion and a circular tapered plunger rod wall connected to the front portion and having a convexly shaped surface. A flexible cup-shaped thermoplastic stopper includes an annular side wall and a continuous front wall connected to the side wall. An exterior surface of the side wall is larger in diameter than the receptacle inside wall. The interior of the stopper includes an inside surface of the front wall and a tapered annular inside wall connected to the annular side wall. This tapered annular inside wall and the inside surface of the front wall are connected and define a cavity which has the tapered tip portion of the plunger rod received therein. Also, the tapered annular inside wall of the stopper has a substantially continuous smooth surface and is inclined in the same direction as the tapered plunger rod wall and is adjacent thereto so that force applied to the shaft portion of the plunger rod in the direction of the descending taper of the tapered plunger rod wall, creates a force component which is directed substantially outwardly from the interface of the tapered plunger rod wall and the tapered annular inside wall wherein the exterior surface applies more pressure to the receptacle inside wall than the initial pressure existing as a result of the exterior surface being larger than the receptacle inside wall. This embodiment also includes cooperating means for maintaining the positional relationship of the stopper and the plunger rod.

Another embodiment of the plunger rod assembly of the present invention consists of a plunger rod and stopper assembly for use with a syringe barrel. The syringe barrel has a substantially cylindrical inside wall with a proximal open end to receive the plunger rod assembly and a distal end adapted to receive and be in fluid communication with fluid delivery means such as a hypodermic needle. A plunger rod includes an elongate shaft portion defining a longitudinal axis and a front portion at the distal end of the shaft portion. A circular forward tapered plunger rod wall intersects the front portion and is tapered outwardly from this intersection along the longitudinal axis. A circular rear tapered plunger rod wall is connected to the forward tapered plunger rod wall and is tapered inwardly from this connection along the longitudinal axis and terminates at a rear portion of this rear tapered plunger rod wall. At least one of the tapered plunger rod walls has a convexly shaped exterior surface. The shaft portion is sufficiently long as to be accessible outside of the syringe barrel. A flexible thermoplastic stopper includes an annular side wall circumscribing a stopper longitudinal axis and a front wall intersecting the stopper longitudinal axis and being integral with the side wall. An annular exterior front surface is formed near the intersection of the front wall and the side wall. A rear edge is formed at the end of the stopper which is opposite to the front wall and this rear edge is integral with the annular side wall. An annular exterior rear surface is formed near the intersection of said side wall and said rear edge. The annular exterior front surface and the annular exterior rear surface are larger in diameter than the syringe barrel inside wall. The interior of the stopper includes a front inside surface of the front wall and a forward tapered annular inside wall intersecting the front inside surface and tapering outwardly from this intersection along the stopper longitudinal axis. This forward tapered annular inside wall is integral with the side wall and adjacent to the forward tapered plunger rod wall so that force applied to the elongate shaft portion, along the longitudinal axis, in the direction of the stopper creates a force component which is directed substantially outwardly from the interface of the forward tapered plunger rod wall and the forward tapered annular inside wall wherein the annular exterior front surface of the stopper applies more sealing pressure to the syringe barrel inside wall than the initial pressure existing as a result of the front surface being larger than the syringe barrel inside wall. A rear tapered annular inside wall is connected to the forward tapered annular inside wall and is tapered inwardly from this connection along the stopper longitudinal axis, terminating near the rear edge. This rear tapered annular inside wall is integral with the side wall and adjacent to the rear tapered plunger rod wall whereby force applied to the elongate shaft portion along its longitudinal axis in a direction away from the stopper creates a force component which is directed substantially outwardly from the interface of the rear tapered plunger rod wall and the rear tapered annular inside wall wherein the annular exterior rear surface applies more sealing pressure to the syringe barrel inside wall than the initial pressure existing as a result of the rear surface being larger than the syringe barrel inside wall.

A further embodiment of the present invention is a syringe assembly. This syringe assembly comprises a syringe barrel, and a plunger rod assembly which includes a plunger rod and a flexible stopper. A syringe barrel having a substantially cylindrical inside wall includes a proximal open end and a distal end adapted to receive and be in fluid communication with fluid delivery means. A plunger rod includes an elongate shaft portion defining a longitudinal axis and having a tapered tip portion at the distal end thereof. This tapered tip portion includes a front portion at the distal end of the tapered tip portion and a circular tapered plunger rod wall connected to the front portion and having a convexly shaped surface. The shaft portion is sufficiently long as to be accessible outside of the syringe barrel. A flexible cup-shaped thermoplastic stopper contained within the syringe barrel. The stopper includes an annular side wall and a continuous front wall connected to the side wall. An exterior surface of the annular side wall is larger in diameter than the syringe barrel inside wall. The interior of the stopper includes an inside surface of the front wall and a tapered annular inside wall connected to the annular side wall. The tapered annular inside wall and the inside surface are connected and define a cavity which has the tapered tip portion received therein. The tapered annular inside wall of the stopper has a substantially continuous smooth surface and is inclined in the same direction as the tapered plunger rod wall and adjacent thereto whereby a force applied to the shaft portion in the direction of descending taper of the tapered plunger rod wall creates a force component which is directed substantially outwardly from the interface of the tapered plunger rod wall and the tapered annular inside wall wherein the exterior surface applies more pressure to the syringe barrel inside wall than the initial pressure existing as a result of the exterior surface being larger than the syringe barrel inside wall. This syringe assembly also includes cooperating means for maintaining the positional relationship of the stopper and the plunger rod.

In accordance with the principles of the present invention a number of advantages and objectives are achieved. The present invention allows an initial interference fit resulting in less normal force between the outside wall of the stopper and the syringe barrel inside wall of an assembled syringe than the interference fit of the components of known syringe assemblies. With the present invention it is only necessary to have an initial interference fit which creates sufficient pressure to contain a fluid in the syringe. The initial interference fit does not have to create enough pressure to allow drawing fluid into the syringe or expelling fluid from the syringe without leakage between the stopper and the syringe barrel since the present invention increases the sealing pressure when a driving force is applied along the plunger rod. This lower initial interference fit results in lower stresses in the stopper when it is assembled in the syringe barrel. Therefore, a thermoplastic syringe stopper may be used since the possibility of compression set, which will adversely affect the function of a syringe with a thermoplastic stopper, is reduced. Accordingly, the present invention provides for the use of a syringe stopper which does not have fillers and vulcanizing agents and is therefore less likely to interact with or contaminate the contents of the syringe. The thermoplastic syringe stopper offers the potential for increased shelf life for drugs which are packaged in the syringe and reduces the potential for adversely affecting the results of laboratory tests involving fluid from the syringe. A reduction in the complexity and the time required for drug compatibility testing is now possible since both the syringe barrel and the stopper can be made of thermoplastic materials. Also, increased productivity is possible due to the lower manufacturing cycle time of injection molded thermoplastics with respect to compression molded rubber parts.

BRIEF DESCRIPTION OF THE DRAWINGS

FIG. 1 is a side elevation view of a preferred plunger rod assembly of the present invention;

FIG. 2 is an enlarged side elevation view of the distal end of a plunger rod of the preferred plunger rod assembly of the present invention;

FIG. 6 is a side elevation view of a syringe assembly containing the preferred plunger rod assembly of the present invention;

FIG. 7 is a partial cross-sectional view of the syringe assembly of FIG. 6 taken along line 7—7 thereof;

DETAILED DESCRIPTION

Figure 3:
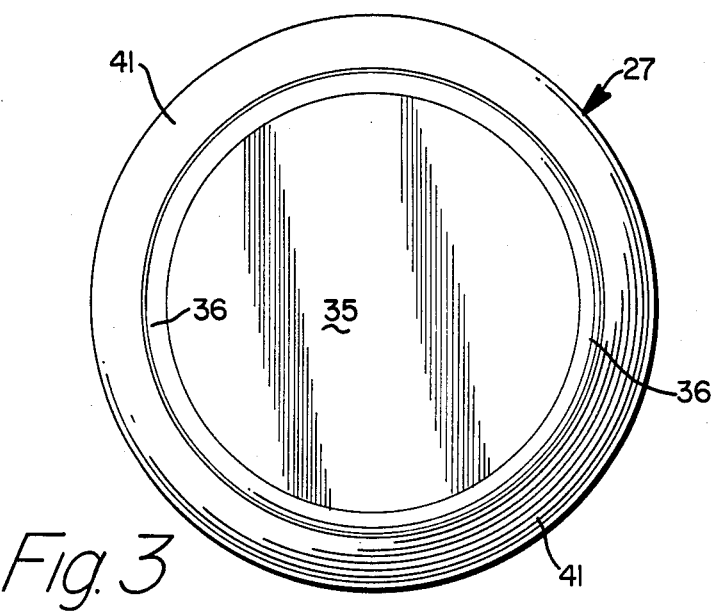
FIG. 3 is an enlarged front elevation view of the distal end of the plunger rod of FIG. 2.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

The plunger rod assembly of the present invention has many uses and one such use is in a syringe as described hereinafter.

Turning to FIGS. 1-5 and to FIG. 1 in particular, a preferred embodiment of the variable sealing pressure plunger rod assembly of the present invention is illustrated. A plunger rod assembly 20 generally includes a flexible stopper 26 and a plunger rod 27.

As best shown in FIGS. 1-3 plunger rod 27 includes an elongate shaft portion 32 defining a longitudinal axis 34. A front portion 35 is located at the distal end of the shaft portion. This front wall is preferably a flat surface in a plane substantially perpendicular to the longitudinal axis. A circular forward tapered plunger rod wall 36 intersects the front portion and tapers outwardly from this intersection along longitudinal axis 34. A circular rear tapered plunger rod wall 37 is connected to the forward tapered plunger rod wall and is tapered inwardly from this connection along longitudinal axis 34 until it terminates at a rear portion 39. Preferably, the rear portion is substantially in a plane intersecting the longitudinal axis. An undercut neck portion 40 is connected to rear portion 39 and to structural flange 41.

A disc shaped member 42 is provided at the proximal end of the elongate shaft portion of the plunger rod. It is desirable that the disc shaped member be substantially perpendicular to longitudinal axis 34 and that it be larger in diameter than the largest dimension of the elongate shaft portion taken in a plane perpendicular to longitudinal axis 34. Disc shaped member 42 is a convenient structure for applying forces to move the plunger rod with respect to the syringe barrel. A central portion 44 of the plunger rod is contained between structural flange 41 and disc shaped member 42. The central portion may assume a variety of cross-sectional shapes including circular or a plus sign shaped rib structure. It is desirable that the central portion be almost as large as the inside diameter of the syringe barrel so that it will assist in keeping the plunger rod assembly concentrically aligned within the syringe barrel. It is preferred that plunger rod 27 be of one piece construction, however, it is within the purview of this invention to include multipiece plunger rods, such as the type used with some prefilled syringes, which are assembled at the time of use.

Figure 4:
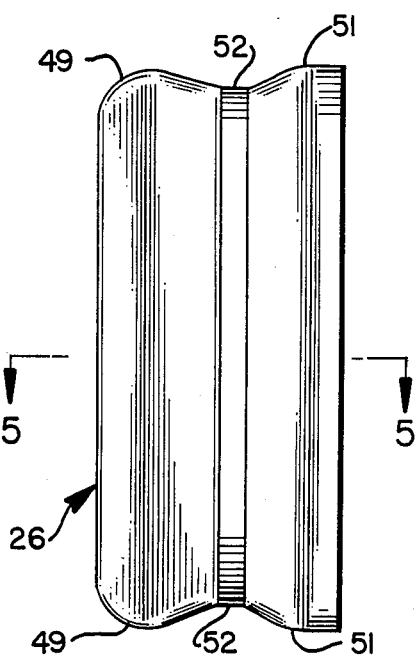
FIG. 4 is an enlarged side elevation view of a flexible stopper of the preferred plunger rod assembly of the present invention.
Figure 5:
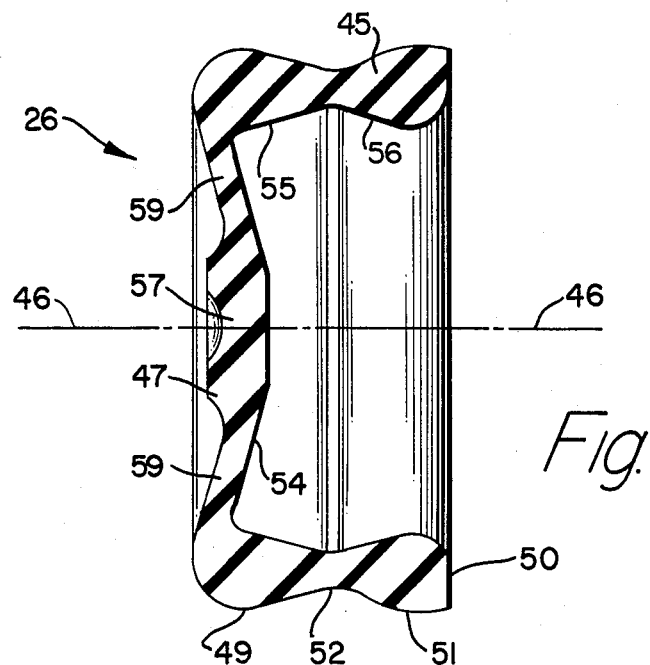
FIG. 5 is an enlarged cross-sectional view of the stopper of FIG. 4 taken along line 5—5.

As best illustrated in FIGS. 4 and 5, flexible stopper 26 includes an annular side wall 45 circumscribing a stopper longitudinal axis 46. A front wall 47 intersects the stopper longitudinal axis and is integral with the side wall. An annular exterior front rib 49 is formed at the intersection of the front wall and the side wall. An annular rear edge 50 is located at the end opposite the front wall and is integral with the annular side wall. An annular exterior rear rib 51 is formed at the intersection of the side wall and the rear edge, with front rib 49 and rear rib 51 being larger in diameter than the syringe barrel inside wall. Also, an annular exterior recess 52 is positioned between and is of smaller diameter than the front rib and the rear rib.

The interior of stopper 26 includes a front inside surface 54 of front wall 47 and a forward tapered annular inside wall 55 which intersects the front inside surface and is tapered outwardly from this intersection along stopper longitudinal axis 46. The forward tapered annular inside wall is inclined at approximately the same angle as forward tapered plunger rod wall 36 and lies adjacent thereto when the stopper and the plunger rod are assembled (as seen by briefly referring to FIGS. 7-9). The interior of stopper 26 also contains a rear tapered annular inside wall 56 connected to the forward tapered annular inside wall and tapered inwardly from this connection along the stopper longitudinal axis and terminating at rear edge 50. The rear tapered annular inside wall is inclined at approximately the same angle as rear tapered plunger rod wall 37 and lies adjacent thereto when the stopper and the plunger rod are assembled. Forward tapered annular inside wall 55 and rear tapered annular inside wall 56 are both preferably integral with annular side wall 45.

Turning now to FIGS. 6–7, the plunger rod assembly of the present invention is incorporated in a syringe barrel 21 having a cylindrical inside wall 22. This syringe barrel is provided with a proximal open end 24 to receive the plunger rod assembly and a distal end adapted to receive and be in fluid communication with fluid delivery means, such as a hypodermic needle 25. The syringe barrel usually includes a flange 29 which is a convenient structure for holding the syringe when the plunger rod is being moved in and out to draw fluids into or expel fluids from the interior of the barrel 30. Many syringe barrels contain a printed scale 31 on the exterior of the barrel so that the user may determine the amount of fluid drawn into or expelled from the syringe.

In use, a hypodermic syringe with needle attached, as shown in FIG. 6, may be filled with liquid medication from a known and available vial, which is not shown. The syringe is filled by piercing and penetrating the pierceable closure of a vial containing the medication with hypodermic needle 25 and manually pushing the plunger rod so that the stopper moves toward the needle thus forcing air into the vial and increasing the air pressure in the vial. Then, with needle tip 28 submerged in the liquid medication, the stopper is withdrawn by pulling the plunger rod so that the medication is drawn through the needle into the syringe. The filled syringe is then used to inject medication into the patient by piercing and penetrating the desired area of the patient's body with the hypodermic needle and then applying manual force to the plunger rod in order to move the stopper along the inside wall of the syringe and force the medication through the needle into the patient.

The pressure exerted by a stopper on the inside wall of a syringe must be large enough to adequately seal this interface in order to prevent liquid medication from escaping while it is being injected into the patient and to prevent air from entering the interior of the syringe barrel when medication is being drawn into the syringe from a medication vial.

Figure 8:
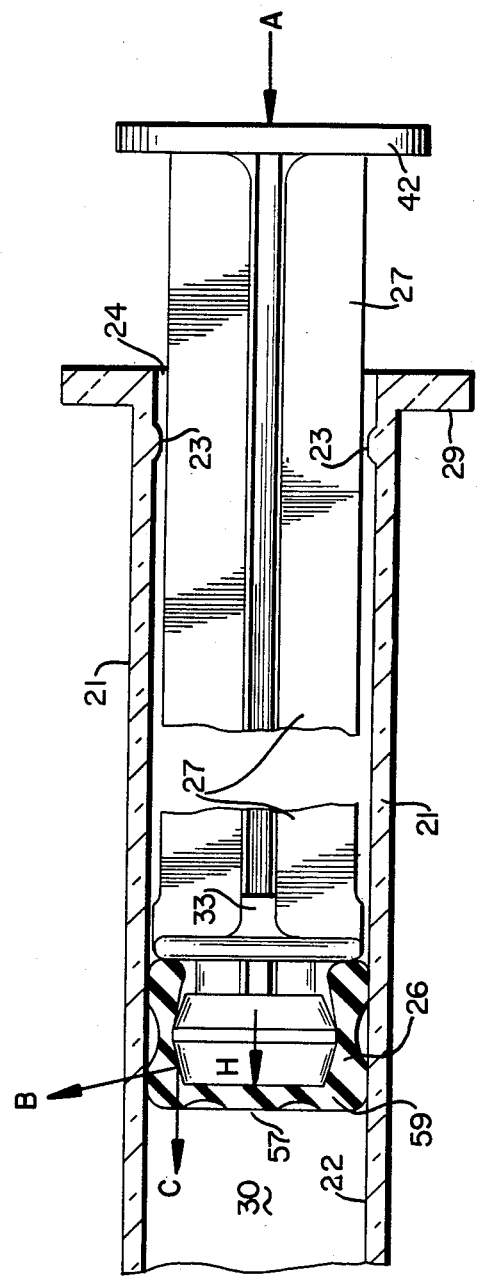
FIG. 8 is an enlarged partial side view of FIG. 7 showing selected forces in action when the preferred plunger rod assembly of the present invention is used to expel fluid from a syringe barrel.
Figure 9:
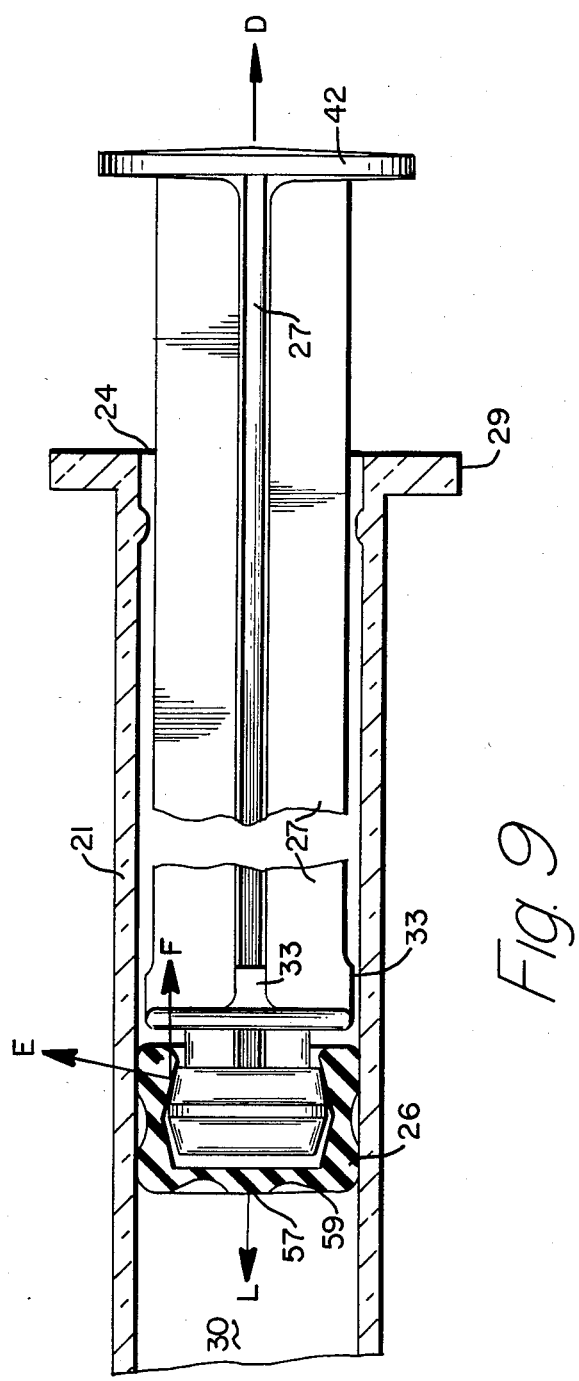
FIG. 9 is an enlarged partial side view of FIG. 7 showing selected forces in action when the present plunger rod assembly of the present invention is used to draw fluid into a syringe barrel.

Referring to FIGS. 1–9 with particular emphasis on FIGS. 8–9, variable sealing pressure plunger rod assembly 20 of the present invention, when assembled in a syringe barrel, functions as follows. When externally applied force A is applied to the elongate shaft portion of the plunger rod, along longitudinal axis 34 in the direction of the stopper, it creates a force component B which is directed substantially outwardly from the interface of forward tapered plunger rod wall 36 and forward tapered annular inside wall 55. As a result of force component B annular exterior front rib 49 applies more sealing pressure to the syringe barrel cylindrical inside wall than the initial pressure existing as a result of the front rib being larger than the syringe barrel inside wall. Simultaneously, a force component C of applied force A moves the stopper and the fluid contained in the syringe along the syringe barrel toward the distal end of the syringe.

When force D is applied to the elongate shaft portion along longitudinal axis 34 in a direction away from the stopper, as seen in FIG. 9, it creates a force component E which is directed substantially outwardly from the interface of rear tapered plunger rod wall 37 and rear tapered annular inside wall 56. As a result of force component E annular exterior rib 51 applies more sealing pressure to the syringe barrel cylindrical inside wall than the initial pressure existing as a result of rear rib 51 being larger than the syringe barrel cylindrical inside wall. At the same time, a force component F of applied force D moves the stopper along the syringe barrel away from the distal end of the syringe thus drawing fluid into the syringe. An interior facing annular ring 23 in the syringe barrel is adapted to engage a step portion 33 on the plunger rod to help prevent the inadvertent removal of the plunger rod assembly from the syringe barrel while filling the syringe with medication.

Front wall 47 of the stopper is concavely shaped and includes a rigid center section 57 and a thinner radially projecting concave front wall portion 59, as more clearly illustrated in FIG. 5. When fluid is being drawn into the syringe a low pressure area is created within the interior of the syringe barrel. The resulting suction force, shown as force component L in FIG. 9, will pull on front wall 47. With the concave structure the suction force pulls on center section 57 which produces a compression force in concave front wall portion 59 which in turn increases the sealing pressure being applied by exterior front rib 49 to the syringe barrel cylindrical inside wall.

It is preferred that front inside surface 54 of the stopper be adjacent to front portion 35 of the plunger rod.

When fluid is being expelled from the syringe, front portion 35 presses against concave center section 57 of the flexible stopper. This pressing force is shown as force component H in FIG. 8. Component H forces the center section outwardly which produces a compression force in concave front wall portion 59 which in turn increases the sealing pressure being applied by exterior front rib 49 to the syringe barrel cylindrical inside wall.

Figure 11:
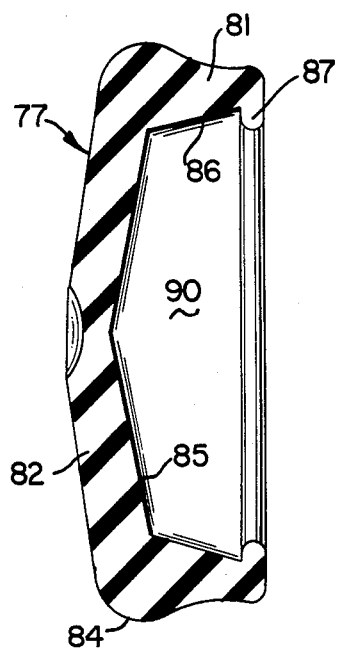
FIG. 11 is an enlarged cross-sectional view of a stopper adapted to fit the plunger rod of FIG. 10.
Figure 12:
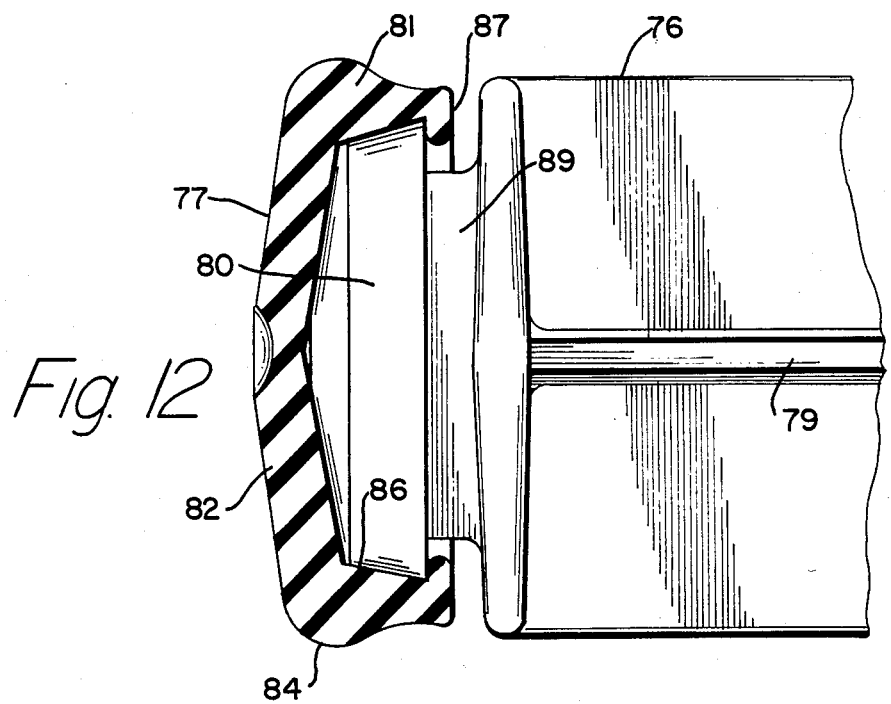
FIG. 12 is an enlarged partial cross-sectional view of an alternative plunger rod assembly using the plunger rod of FIG. 10 and the stopper of FIG. 11.
Figure 14:
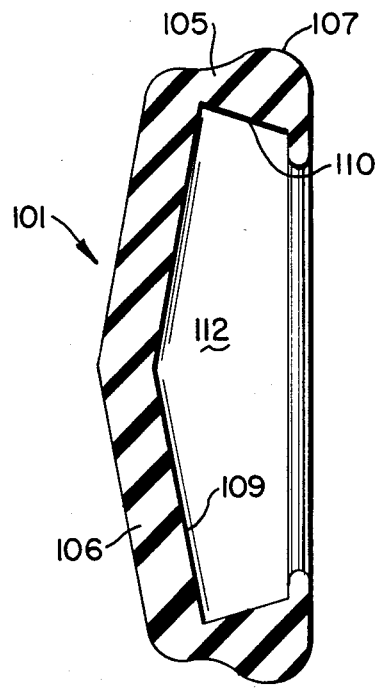
FIG. 14 is an enlarged cross-sectional view of a stopper adapted to fit the plunger rod FIG. 13.

There are many cases where a convexly shaped stopper, as illustrated in FIGS. 11, 12 and 14, is preferred to reduce the amount of medication lost in the syringe. In these cases the suction force encountered when fluid is being drawn into the syringe will pull on the front wall of a convexly shaped stopper tending to pull the exterior front rib away from the syringe barrel cylindrical inside wall. This tendency can be substantially minimized by increasing the stiffness of the stopper front wall by making it thicker or by supplying internal structural ribs. Also, medication loss may be reduced in the concave stopper structure by enlarging the rigid center section in a direction along the stopper longitudinal axis.

It is preferred that both forward tapered plunger rod wall 36 and rear tapered plunger rod wall 37 have a substantially continuous smooth surface so that outwardly directed forces B and E, respectively, are transmitted uniformly to the stopper ribs, thus tending to provide uniform sealing pressure between the stopper ribs and the cylindrical inside wall.

Figure 10:
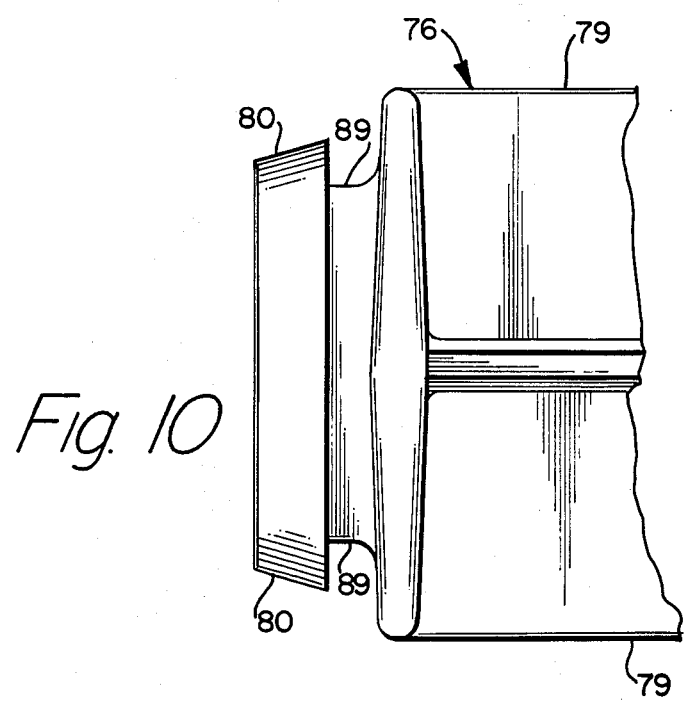
FIG. 10 is an enlarged side elevation view of the distal end of a plunger rod of an alternative embodiment of a plunger rod assembly of the present invention.

FIGS. 10-12 show an alternative embodiment of the plunger rod assembly of the present invention. This embodiment is similar to the previously described preferred embodiment except that the plunger rod tip and the stopper inside wall are only tapered in one direction. Here the plunger rod assembly comprises a plunger rod 76 and a flexible cup-shaped stopper 77. Plunger rod 76 includes a rigid elongate shaft portion 79 having a circular tapered tip portion 80 at the distal end thereof. The tapered tip is smallest at the distal end of the plunger rod and is tapered outwardly along the elongate shaft portion.

Stopper 77 includes an annular side wall 81, a front wall 82 connected to the side wall, and an exterior surface 84 of the annular side wall which is larger in diameter than the receptacle inside wall. The interior of stopper 77 includes an inside surface 85 of front wall 82, a tapered annular inside wall 86 connected to the annular side wall and the inside surface. Tapered annular inside wall 86 and inside surface 85 define a cavity 90 which has the tapered tip portion received therein as can be seen in FIG. 12. Tapered annular inside wall 86 is inclined at approximately the same angle as tapered tip portion 80 and is adjacent thereto, when assembled. When the plunger rod assembly of this embodiment is placed in a receptacle, such as a syringe, and a driving force is applied along elongate shaft portion 79 in the direction of stopper 77, a force component is created. This force component is directed substantially outwardly from the interface of tapered tip portion 80 and tapered annular inside wall 86, in a manner similar to the previously described embodiment. The result is that exterior surface 84 applies more sealing pressure to the receptacle inside wall than the pressure existing as a result of the exterior surface being larger than the receptacle inside wall. Simultaneously, a component of the applied driving force along the elongate shaft portion in the direction of the stopper moves the stopper and the fluid contained in the receptacle in the direction of this force component. No outwardly directed force component is created unless the plunger rod assembly is in a receptacle which offers resistance to the motion of the stopper. This resistance will be created by making the receptacle inside diameter smaller than the stopper outside diameter.

In order to maintain the positional relationship of the stopper and the plunger rod and to hold tapered tip portion 80 adjacent to tapered annular inside wall 86 flexible flange 87 and groove 89 are provided. Flexible flange 87 is connected to and extends inwardly from annular side wall 81 at the end opposite front wall 82. Groove 89 in the plunger rod is sized and shaped to accept flange 87 which is received therein. The groove is positioned inwardly adjacent to tapered tip portion 80.

Figure 13:
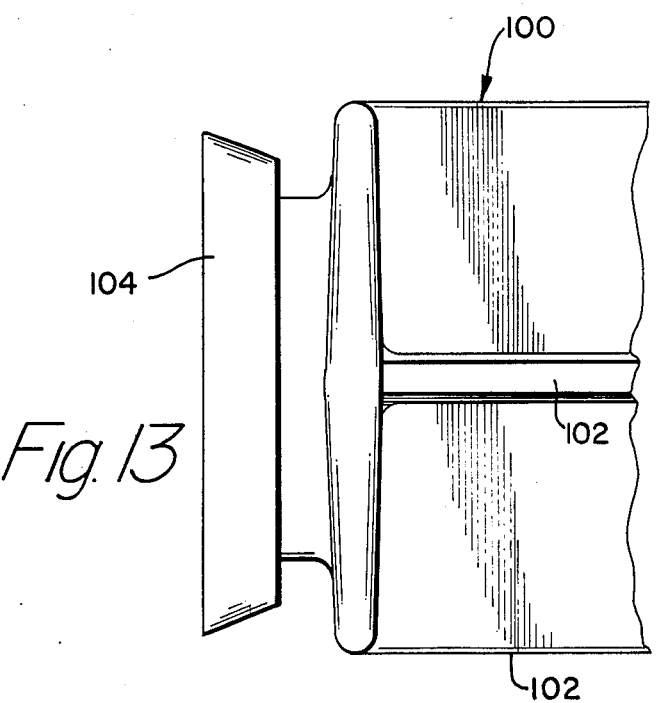
FIG. 13 is an enlarged side elevation view of the distal end of a plunger rod of another alternative embodiment of a plunger rod assembly of the present invention.

FIGS. 13-14 show another alternative embodiment of the plunger rod assembly of the present invention. This alternative embodiment is similar to the embodiment described by FIGS. 10-12 except that, as will be described, the direction of the tapered surfaces is reversed. Here the plunger rod assembly consists of a plunger rod 100 and a flexible cup-shaped stopper 101. Plunger rod 100 includes a rigid elongate shaft portion 102 having a circular tapered tip portion 104 at the distal end thereof. The diameter of the tapered tip is largest at the distal end of the plunger rod and is tapered inwardly along the elongate shaft portion.

Stopper 101 includes an annular side wall 105, a front wall 106 connected to the side wall, and an exterior surface 107 of the annular side wall which is larger in diameter than the inside wall of a receptacle, such as a syringe, into which the stopper fits. The interior of stopper 101 includes an inside surface 109 of front wall 106, a tapered annular inside wall 110 connected to the annular side wall and the inside surface. Tapered annular inside wall 110 and inside surface 109 define a cavity 112. The assembly of plunger rod 100 and stopper 101 is not shown, but is similar to the previous embodiments. When these components are assembled cavity 112 has tapered tip portion 104 received therein. Tapered annular inside wall 110 is inclined at approximately the same angle as tapered tip portion 104 and is adjacent thereto. When the receptacle, such as a syringe, and when a driving force is applied along the elongate shaft portion, in a direction away from the stopper, exterior surface 107 applies more pressure to the receptacle inside wall than the pressure existing as a result of the exterior surface being larger than the receptacle inside wall.

Turning to FIGS. 15-19, another preferred embodiment of the variable sealing pressure plunger rod assembly of the present invention is illustrated. A plunger rod assembly 200 generally includes a flexible thermoplastic stopper 201 and a plunger rod 202 for use in a syringe barrel 203 having a cylindrical inside wall 206. This syringe barrel is similar to the syringe barrel of FIGS. 6-9 and is provided with a proximal open end 213 to receive the plunger rod assembly and a distal end (not shown) adapted to receive and be in fluid communication with fluid delivery means such as a hypodermic needle (not shown).

Figure 15:
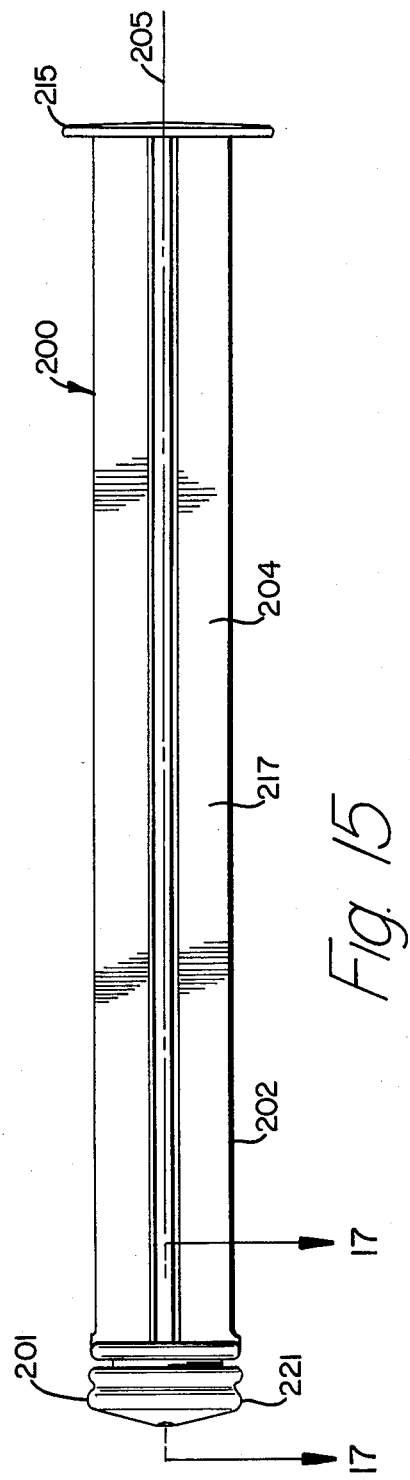
FIG. 15 is a side elevation view of another preferred plunger rod assembly of the present invention.
Figure 16:
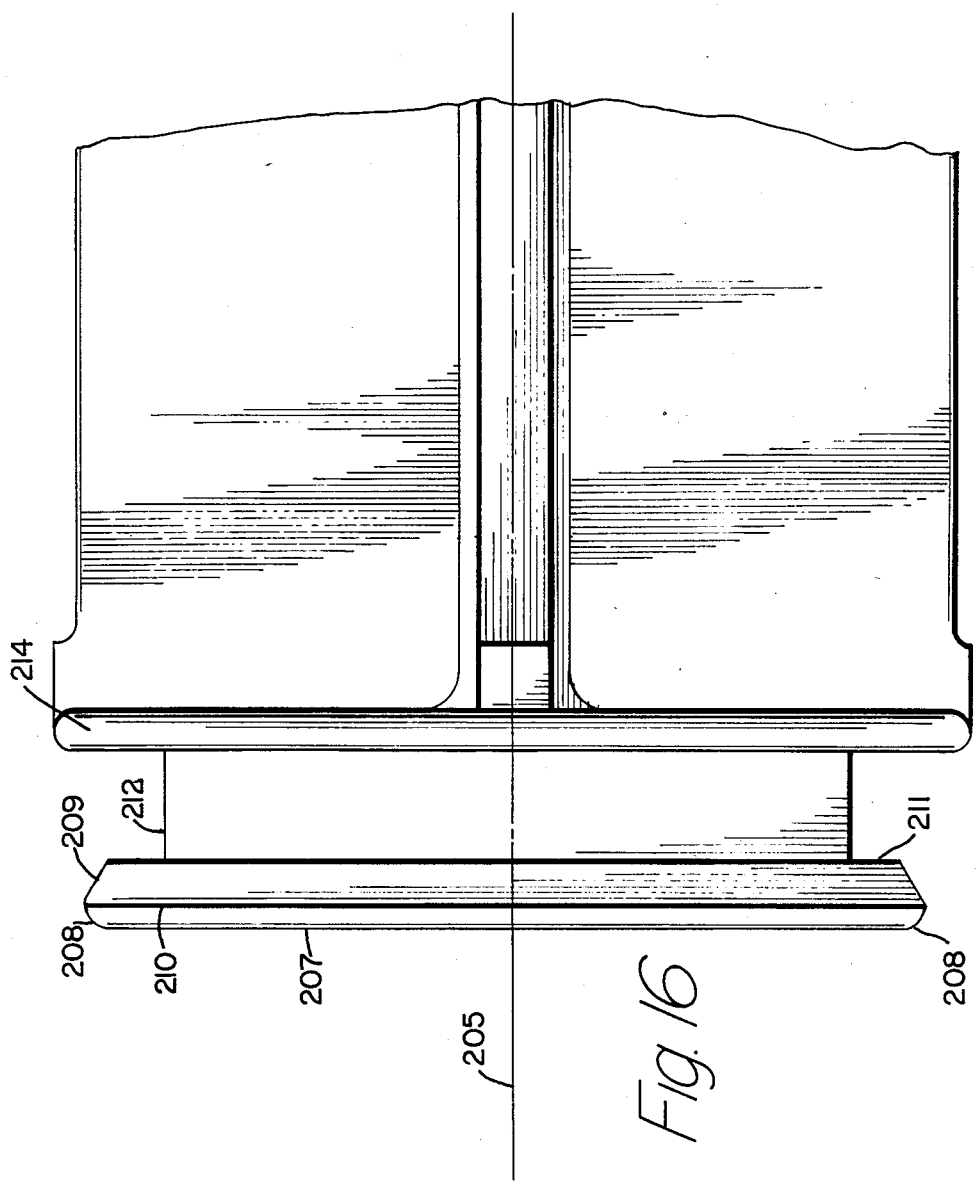
FIG. 16 is an enlarged side elevation view of the distal end of the plunger rod of FIG. 15.
Figure 17:
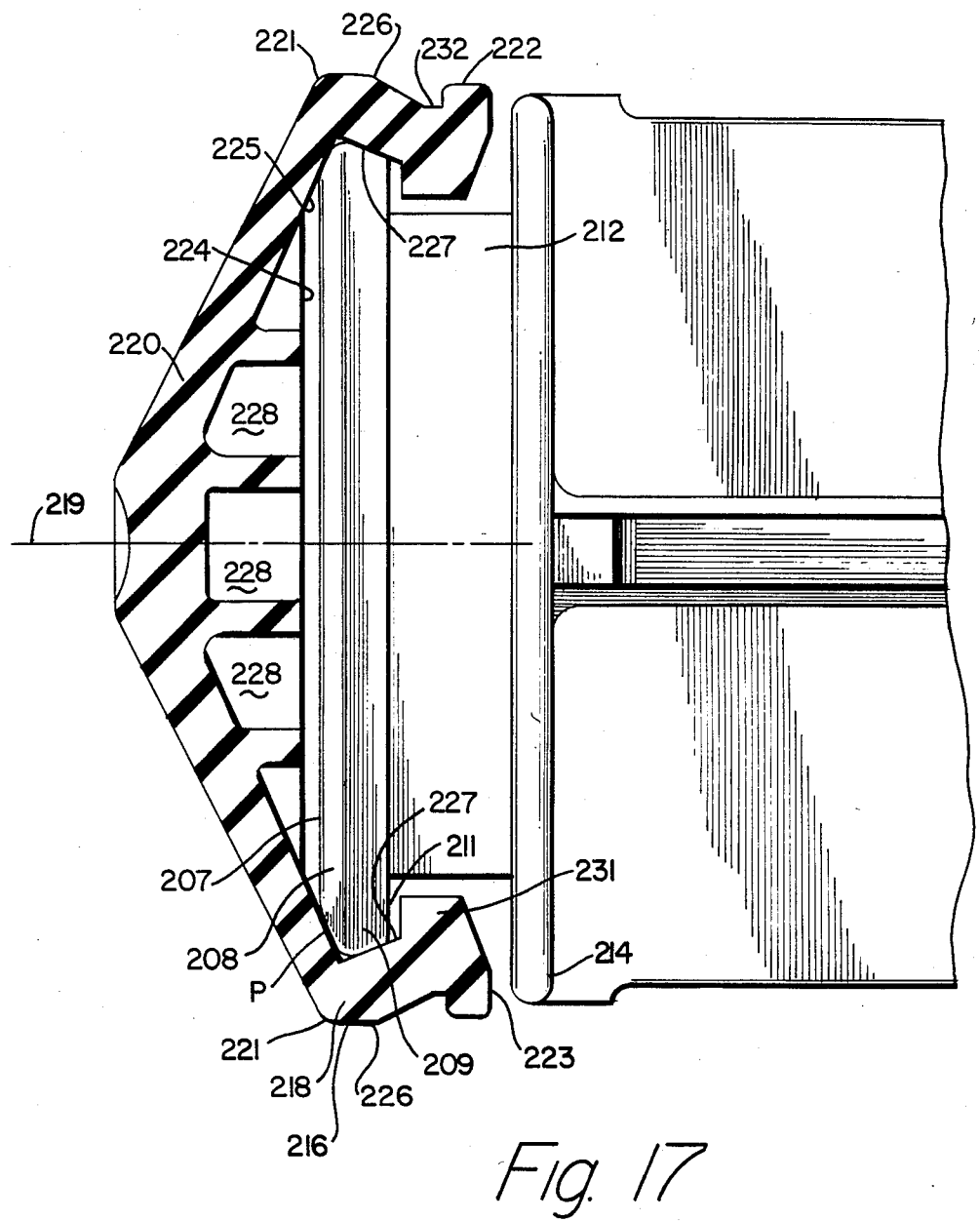
FIG. 17 is an enlarged partial cross-sectional view of the distal end of the plunger rod assembly of FIG. 15 taken along lines 17—17.

As best illustrated in FIGS. 15-17 plunger rod 202 includes an elongate shaft portion 204 defining a longitudinal axis 205. A front portion 207 is located at the distal end of the shaft portion. This front portion includes a preferably flat surface in a plane substantially perpendicular to the longitudinal axis. A circular forward tapered plunger rod wall 208 having a convexly shaped surface intersects the front portion and tapers outwardly from this intersection along longitudinal axis 205. A circular rear tapered plunger rod wall 209 connected to the forward tapered plunger rod wall at connection line 210 and is tapered inwardly from the connection line along longitudinal axis 205 until it terminates at a rear portion 211. The rear portion is substantially in a plane intersecting the longitudinal axis. An undercut neck portion 212 is connected to rear portion 211 and to a structural flange 214.

It should be noted that forward tapered plunger rod wall 208 is similar to forward tapered plunger rod wall 36 of the embodiment of FIGS. 1–5 except that forward tapered plunger rod wall 208 has a convexly shaped surface rather than the relatively straight surface of plunger rod wall 36. It is within the purview of this embodiment to include various degrees of convexity from slight, as formed by a large radius, to large, as formed by a small radius. The embodiment illustrated has a convex surface generated by a radius which is as long as the distance between front portion 207 and connection line 210 measured along longitudinal axis 205.

A disc shaped member 215 is provided at the proximal end of the elongate shaft portion of the plunger rod. Disc shaped member 215 is a convenient structure for applying forces to move the plunger rod with respect to the syringe barrel. A central portion 217 of the plunger rod is contained between structural flange 214 and disc shaped member 215. It is desirable that the central portion be almost as large as the inside diameter of the syringe barrel so that it will assist in keeping the plunger rod assembly concentrically aligned within the syringe barrel.

As best illustrated in FIGS. 15 and 17, flexible thermoplastic stopper 201 includes an annular side wall 218 circumscribing a stopper longitudinal axis 219. A continuous front wall 220 intersects the stopper longitudinal axis and is integral with the side wall. An annular exterior front surface 221 is formed at the intersection of the front wall and the side wall. An annular rear edge 223 is located at the end opposite the front wall and is integral with the annular side wall. An annular exterior rear surface 226 is formed in the side wall adjacent to and on the distal side of annular exterior front surface 221 so that annular rear surface 226 is nearer to rear edge 223 than annular exterior front surface. It should be noted that the annular exterior front surface 221 and the annular exterior rear surface 226 are both part of a front rib 216. However, it is within the purview of this invention to include a stopper structure wherein the annular exterior front surface and the annular exterior rear surface can be part of separate ribs, similar to the two rib embodiment of FIGS. 4 and 5.

An annular exterior rear rib 222 is formed at the intersection of the side wall and the rear edge. The front rib which includes annular exterior rear surface 226 and annular exterior front surface 221 is larger in diameter than the syringe barrel inside wall. Also, an annular exterior recess 232 is positioned between and is of smaller diameter than front rib 216 and the rear rib 222. As will be explained in more detail hereinafter, rear rib may or may not be larger in diameter than the syringe barrel inside diameter. In the instant embodiment, the rear rib is preferably smaller in diameter than front surface 221 and rear surface 226, but larger than the inside diameter of syringe barrel.

It is also within the purview of this invention to include a shorter stopper, without the rear rib and the adjacent annular recess, so that the annular exterior rear surface is formed at the end opposite the front wall, near the intersection of the side wall and a rear edge.

The interior of stopper 201 includes a front inside surface 224 of front wall 220 and a forward tapered annular inside wall 225 which intersects the front inside surface and is tapered outwardly from this intersection along stopper longitudinal axis 219. The forward tapered annular inside wall is inclined in the same direction as the forward tapered plunger rod wall so that their respective slopes have the same mathematical sign. Forward tapered annular inside wall 225 is preferably adjacent to forward tapered plunger rod wall 208 when the stopper and the plunger rod are assembled (as illustrated by referring to FIGS. 17–19). The interior of stopper 201 also contains a rear tapered annular inside wall 227 connected to the forward tapered annular inside wall and tapered inwardly from this connection along the stopper longitudinal axis. The rear tapered annular inside wall is inclined in the same direction as rear tapered plunger rod wall 209 and preferably lies adjacent thereto when the stopper and the plunger rod are assembled. Forward tapered annular inside wall 225 and rear tapered annular inside wall 229 are both preferably integral with annular side wall 218. Front wall 220 also includes recesses 228 on the proximal side thereof. These recesses are provided so that less material is used in the fabrication of the stopper and to provide more uniform wall thicknesses throughout the stopper structure.

Figure 18:
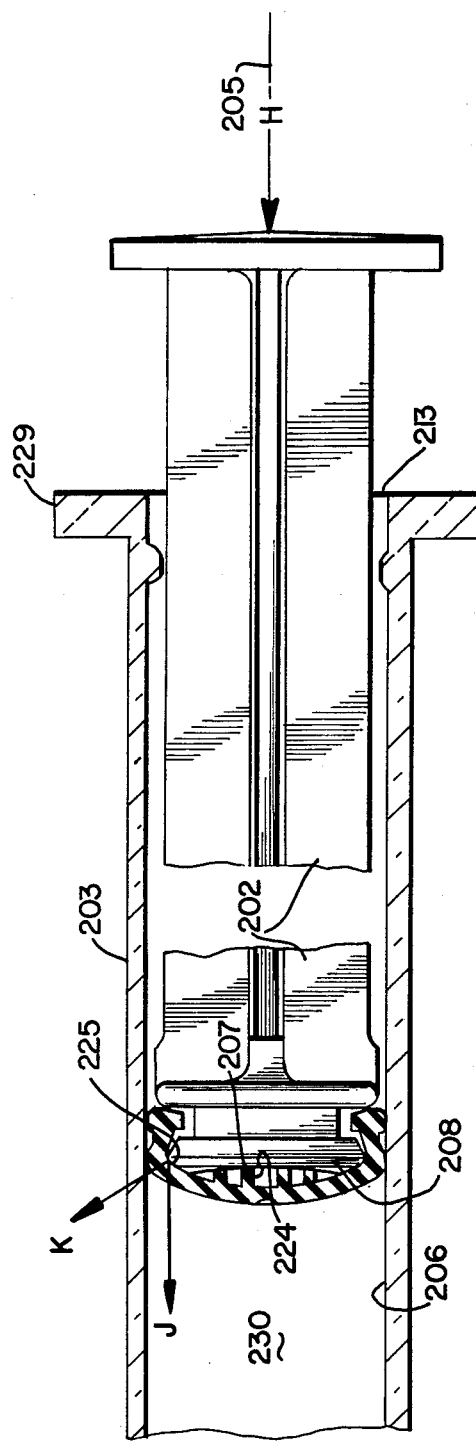
FIG. 18 is an enlarged partial cross-sectional view showing selected forces in action when the plunger rod assembly of FIG. 15 is used with a syringe barrel to expel fluid from the syringe barrel.
Figure 19:
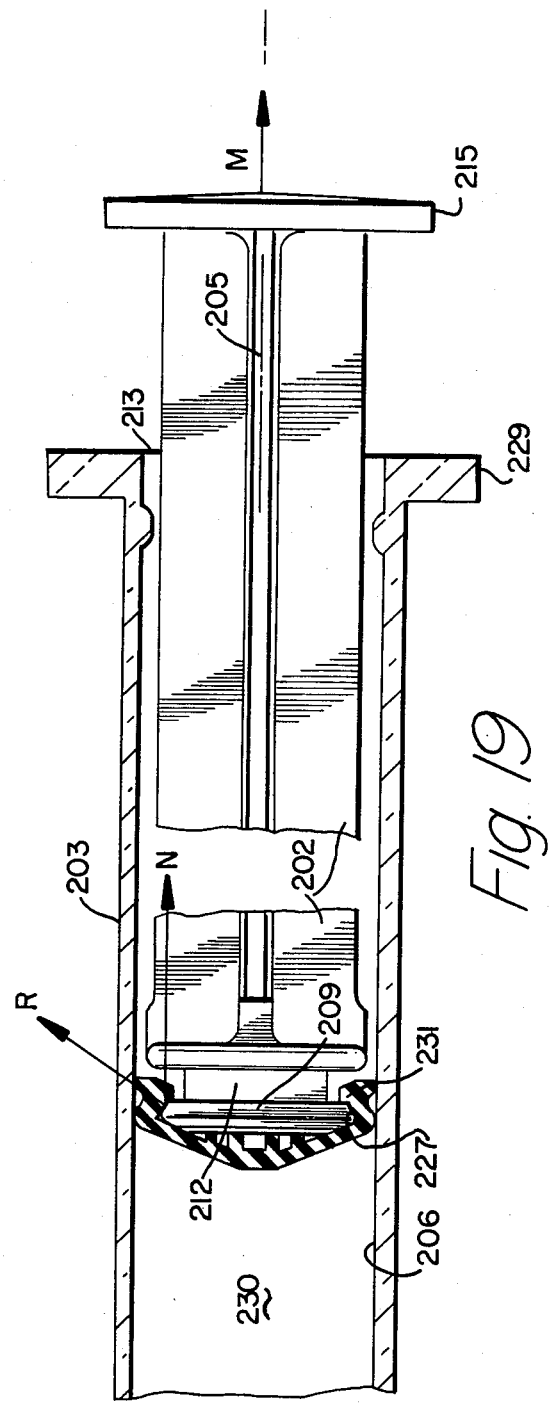
FIG. 19 is an enlarged partial cross-sectional view showing selected forces in action when the plunger rod assembly of FIG. 15 is used with a syringe barrel to draw fluid into the syringe barrel.

Turning now to FIGS. 18–19, the plunger rod assembly of the present invention is incorporated in syringe barrel 203. The syringe barrel preferably includes a flange 29 which is a convenient structure for holding the syringe when the plunger rod is being moved in and out to draw fluids into or expel fluids from the interior 230 of barrel 203. In use, a hypodermic syringe with needle (not shown) attached, may be filled with liquid medication from a known and available vial using methods described hereinabove.

Referring to FIGS. 17–19, the variable sealing pressure plunger rod assembly of the present embodiment, when assembled in a syringe barrel, functions as follows. When externally applied force H is applied to the elongate shaft portion of the plunger rod, along longitudinal axis 205 in the direction of the stopper, it creates a force component K which is directed substantially outwardly from the interface of forward tapered plunger rod wall 208 and forward tapered annular inside wall 225.

It should be noted that before the distal portion of plunger rod assembly 200 is placed in the syringe barrel, the area of possible contact between forward tapered inside wall 225 and convexly shaped forward tapered plunger rod wall 208 (shown as P in FIG. 17) tends to be on the portion of the forward tapered plunger rod wall which is approximately centrally located along the convex surface. However, because the syringe barrel inside diameter is smaller than annular exterior front surface 221 of the stopper, the stopper is forced toward the convexly shaped forward tapered plunger rod wall, causing stopper contact over more of the area of the forward tapered plunger rod wall. This contact area is further enhanced when force H is applied to the plunger rod because frictional forces between inside wall 206 of the syringe barrel and annular exterior front surface 221 of the stopper tend to pull the stopper toward the distal end of the plunger rod further promoting contact around more of the surface of the convexly shaped plunger rod wall, as best illustrated in FIG. 18 through the line of action of force component K.

As a result of force component K, annular exterior front surface 221 applies more sealing pressure to the syringe barrel cylindrical inside wall than the initial pressure existing as a result of the annular exterior front surface of the stopper being larger in diameter than the syringe barrel inside wall. Simultaneously, a force component J of applied force H moves the stopper and the fluid contained in the syringe along the syringe barrel toward the distal end of the syringe. It should also be noted that the fluid pressure in the interior of the barrel will tend to force front wall 220 of the stopper toward the distal end of the plunger rod. However, this motion is limited by contact between front inside surface 224 of the stopper and front portion 207 of the plunger rod. Also, because of the convex shape of front wall 220, the slight motion of the front wall of the stopper toward the plunger rod is believed to provide compressive forces in the front wall which tend to increase the pressure exerted on the inside wall of the syringe barrel by annular exterior front surface 221 of the stopper.

When force M is applied to the elongate shaft portion along longitudinal access 205 in a direction away from the stopper, as illustrated in FIG. 19, it creates a force component R which is directed substantially outwardly from the interface of rear tapered plunger rod wall 209 and rear tapered annular inside wall 227. As a result of force component R annular exterior rear surface 226 of the stopper applies more sealing pressure to the syringe barrel cylindrical inside wall than the initial pressure existing as a result of annular exterior rear surface 226 being larger than the syringe barrel cylindrical in side wall. At the same time, a force component N of applied force M moves the stopper along the syringe barrel away from the distal end of the syringe, thus drawing fluid into the syringe.

While force component M is being applied to plunger rod 202, the lower pressures in interior 230 of barrel 203 will tend to promote the separation of the stopper and the plunger rod. However, inwardly facing flange portion 231 on the stopper projects radially inwardly from said stopper into undercut neck portion 212 of the plunger rod to assist in preventing the disengagement of the plunger rod from the stopper. Also, while force component M is being applied to the plunger rod, annular exterior rib 222 will, preferably, press against the inside wall of the syringe barrel tending to prevent flange portion 231 from being pulled out of the undercut neck portion of the plunger rod by the lower forces in the interior of the barrel.

Figure 20:
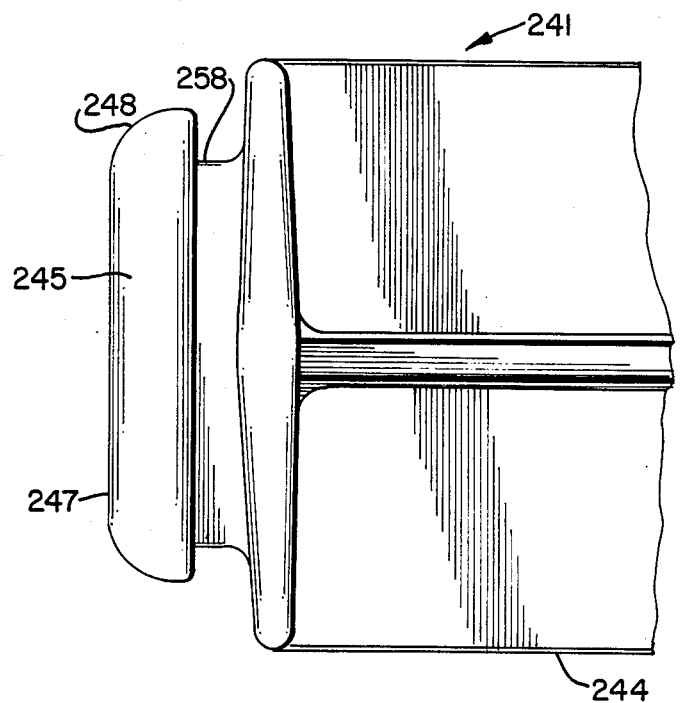
FIG. 20 is an enlarged side elevation view of the distal end of a plunger rod of another embodiment of the present invention.
Figure 21:
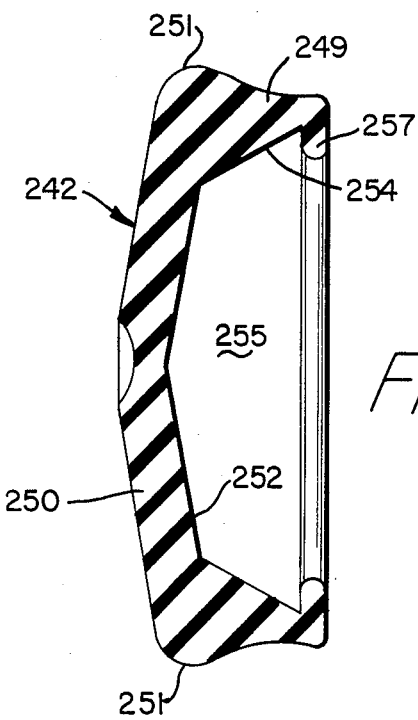
FIG. 21 is an enlarged cross-sectional view of a stopper adapted to fit the plunger rod of FIG. 20.
Figure 22:
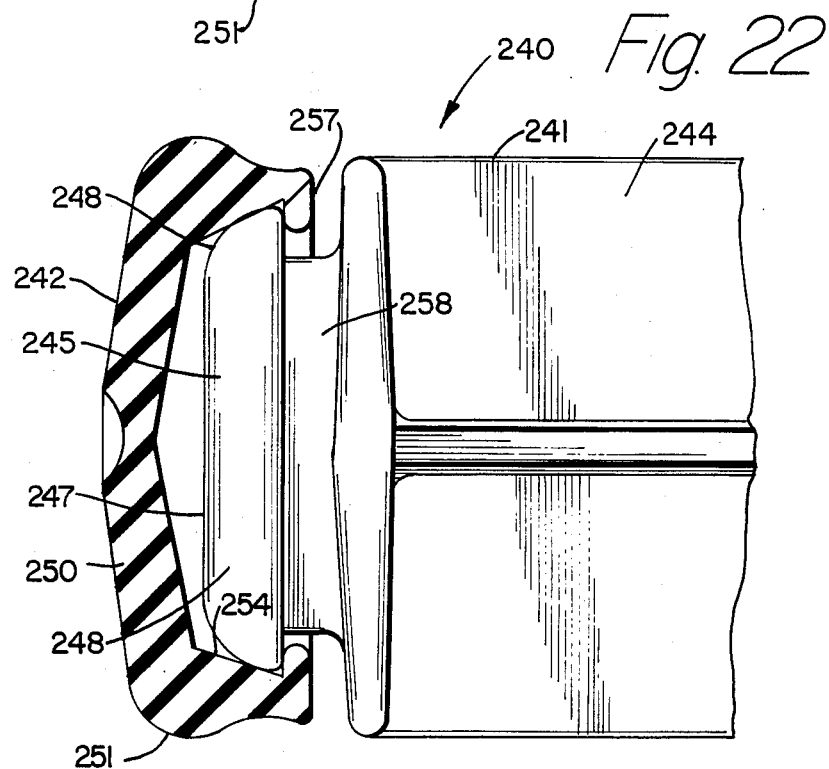
FIG. 22 is an enlarged partial cross-sectional view of an alternative plunger rod assembly using the plunger rod of FIG. 20 and the stopper of FIG. 21.

FIGS. 20–22 show an alternative embodiment of the plunger rod assembly of the present invention. This embodiment is similar to the previously described embodiment of FIGS. 15–19 except that the plunger rod tip and the stopper inside wall are only tapered in one direction in this embodiment. Here the plunger rod assembly 240 comprises a plunger rod 241 and a flexible thermoplastic cup-shaped stopper 242 for use with a syringe barrel (not shown). Plunger rod 241 includes a rigid elongate shaft portion 244 having a tapered tip portion 245 at the distal end thereof. The tapered tip portion includes a front portion 247 at the distal end thereof and a circular tapered plunger rod wall 248 having a convexly shaped surface intersecting the front portion. The tapered tip is smallest at the distal end and is tapered outwardly along the tapered tip portion.

Cup-shaped stopper 242 includes an annular side wall 249, a continuous front wall 250 connected to the side wall, and an exterior surface 251 of the annular side wall which is larger in diameter than the syringe barrel inside wall. The interior of stopper 242 includes an inside surface 252 of front wall 250, a tapered annular inside wall 254 connected to the annular side wall and the inside surface. Tapered annular inside wall 254 and inside surface 252 define a cavity 255 which has the tapered tip portion received therein, as can be seen in FIG. 22. Tapered annular inside wall 254 has a substantially continuous smooth surface and is inclined in the same direction as tapered plunger rod wall 248 and is adjacent thereto, when assembled. When the plunger rod assembly of this embodiment is placed in a syringe barrel and a driving force is applied along the elongate shaft portion in the direction of stopper 242, a force component is created. This force component is directed substantially outwardly from the interface tapered plunger rod wall 248 and tapered annular inside wall 254, in a manner similar to the previously described embodiment. The result is that exterior surface 251 applies more sealing pressure to the syringe barrel inside wall than the pressure existing as a result of the exterior surface being larger than the syringe barrel inside wall. Simultaneously, a component of applied driving force along the elongate shaft portion, in the direction of the stopper, moves the stopper and the fluid contained in the receptacle in the direction of this force component.

In order to maintain the positional relationship of the stopper and the plunger rod, and to hold circular tapered plunger rod wall 248 adjacent to tapered annular inside wall 254, flexible flange 257 and groove 258 are provided. Flexible flange 257 is connected to and extends inwardly from annular side wall 249 of the stopper, at the end opposite front wall 250. Groove 258 in the plunger rod is sized and shaped to accept flange 257 which is received therein. The groove is positioned inwardly adjacent to tapered tip portion 245.

Figure 23:
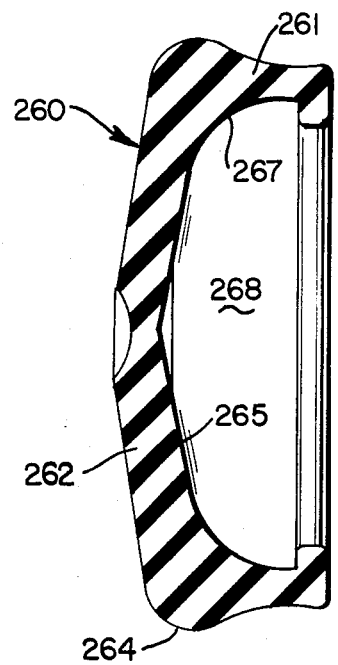
FIG. 23 is an enlarged cross-sectional view of another embodiment of a stopper adapted to fit the plunger rod of FIG. 20.

FIG. 23 shows another alternative embodiment of a stopper for use in a plunger rod assembly with the plunger rod of FIG. 20. This alternative embodiment includes a stopper which is similar to the stopper of FIG. 21 except that, as will be described, the tapered annular inside wall has a concavely shaped surface. Here, stopper 260 includes an annular side wall 261, a front wall 262 connected to the side wall, and an exterior surface 264 of the annular side wall which is larger in diameter than the inside wall of the syringe barrel, into which the stopper fits. The interior of stopper 260 includes an inside surface 265 of front wall 262, a tapered annular inside wall 267 connected to the annular side wall and the inside surface. Tapered annular inside wall 267 and inside surface 265 define a cavity 268. The assembly of a plunger rod, such as the plunger rod of FIG. 20, and stopper 260 of this embodiment is not shown, but is similar to previous embodiments. When these components are assembled cavity 268 has the tapered tip portion of the stopper received therein. Tapered annular inside wall 267 is inclined in the same direction as the tapered plunger rod wall and is adjacent thereto. When a plunger rod assembly, using stopper 260, is in a syringe barrel and a driving force is applied along the plunger rod, in a direction toward the stopper, exterior surface 264 applies more pressure to the syringe barrel inside wall than the pressure existing as a result of the exterior surface being larger than the syringe barrel inside wall.

Figure 25:
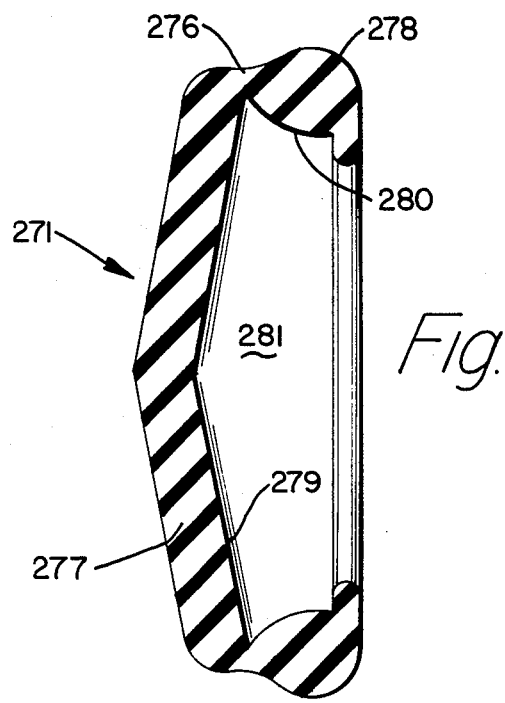
FIG. 25 is an enlarged cross-sectional view of a stopper adapted to fit the plunger rod of FIG. 24.
Figure 24:
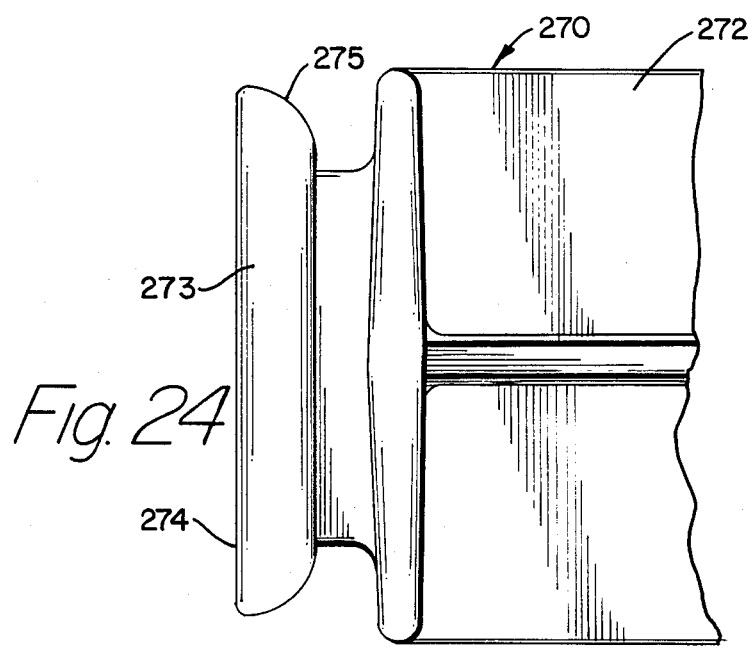
FIG. 24 is an enlarged side elevation view of the distal end of a plunger rod of still another alternative embodiment of a plunger rod assembly of the present invention.

FIGS. 24–25 show another alternative embodiment of the plunger rod assembly of the present invention. This alternative embodiment is similar to the embodiment illustrated in FIGS. 20–22 except that, as will be described, the direction of the tapered surfaces is reversed. Here the plunger rod assembly consists of a plunger rod 270 and a flexible cup-shaped stopper 271. Plunger rod 270 includes an elongate shaft portion 272 having a tapered tip portion 273 at the distal end thereof. The tapered tip portion includes a front portion 274 at the distal end thereof and a circular tapered plunger rod wall 275 having a convexly shaped surface intersecting the front portion. The diameter of the tapered tip is largest at front portion 274 and is tapered inwardly along the tapered tip portion.

Stopper 271 includes an annular side wall 276, a front wall 277 connected to the side wall, and an exterior surface 278 of the annular side wall which is larger in diameter than the inside wall of a receptacle, such as a syringe, into which the stopper fits. The interior of stopper 271 includes an inside surface 279 of front wall 277 and a tapered annular inside wall 280 connected to the annular side wall and to the inside surface. Tapered annular inside wall has a convexly shaped surface. Tapered annular inside wall 280 and inside surface 279 define a cavity 281.

The assembly of plunger rod 270 and stopper 271 is not shown, but is similar to the embodiment of FIGS. 20–22. When these componets are assembled cavity 281 has tapered tip portion 273 received therein. Tapered annular inside wall 280 is inclined in the same direction as tapered plunger rod wall 275 and is adjacent thereto and assembled. When the plunger rod and stopper assembly of the present embodiment is placed in a receptacle, such as a syringe, and when a driving force is applied along the elongate shaft portion, in a direction away from the stopper, exterior surface 278 applies more pressure to the receptacle inside wall than the pressure existing as a result of exterior surface 278 being larger than the receptacle inside wall.

Although the plunger rod assembly of the present invention is being described for use with a circular syringe barrel or circular receptacle it is understood that the principles of the present invention also apply for a use in a noncircular receptacle or barrel.

Syringe barrels are usually made of plastic such as polypropylene, or glass. It is common practice to lubricate the interior of the syringe barrel and/or the exterior of known stoppers with medical grade lubricant such as silicone lubricant. The lubricant allows the stopper to move freely along the interior of the barrel even when there is no liquid in the interior of the syringe barrel. The plunger rod may be constructed of a wide variety of materials since, in most applications, adequate strength and reasonable cost are the major considerations. Possible plunger rod materials include polypropylene, polyethylene and polystyrene. Certain thermoplastic materials, preferably having a durometer reading of from 30 to 90 on the Shore A scale, may be used in manufacturing a thermoplastic stopper. Preferred stopper materials include, but are not limited to, polyurethane, polyester, polyolefin elastomers, polystyrene-polybutadiene-polystyrene, polyamide and polyamide block amide. Since the plunger rod assembly of this invention is preferably sterile, when used in medical applications, all materials should be chosen to accommodate the sterilization process.

Thus, there has been provided in accordance with the present invention a method and an apparatus for moving fluid along a conduit and more particularly a variable sealing pressure plunger rod assembly useful in a syringe in which the stopper may be constructed of thermoplastic material.

What is claimed is:

1. A plunger rod assembly for use with a receptacle having a substantially cylindrical inside wall and provided with means for receiving the plunger rod assembly and means for fluid communication with the exterior of the receptacle comprising:

a plunger rod including an elongate shaft portion defining a longitudinal axis and having a tapered tip portion at the distal end thereof, said tapered tip portion including a front portion at the distal end thereof and a circular tapered plunger rod wall connected to said front portion and having a convexly shaped surface;

a flexible cup-shaped thermoplastic stopper including an annular side wall, a continuous front wall connected to said side wall, an exterior surface of said annular side wall being larger in diameter than the receptacle inside wall, an inside surface of said front wall, a tapered annular inside wall connected to said annular side wall, said tapered annular inside wall and said inside surface being connected and defining a cavity which has said tapered tip portion received therein, said tapered annular inside wall having a substantially continuous smooth surface, said tapered annular inside wall being inclined in the same direction as said tapered plunger rod wall and adjacent thereto whereby force applied to said shaft portion in the direction of descending taper of said tapered plunger rod wall creates a force component which is directed substantially outwardly from the interface of said tapered plunger rod wall and said tapered annular inside wall wherein said exterior surface applies more pressure to the receptacle inside wall than the initial pressure existing as a result of said exterior surface being larger than the receptacle inside wall; and cooperating means for maintaining the positional relationship of said stopper and said plunger rod.

2. The plunger rod assembly of claim 1 wherein said front wall of said stopper is concavely shaped.

3. The plunger rod assembly of claim 1 wherein said front wall of said stopper is convexly shaped.

4. The plunger rod assembly of claim 1 wherein said front portion of said plunger rod includes a flat surface in a plane substantially perpendicular said longitudinal axis.

5. The plunger rod assembly of claim 1 wherein said front inside surface of said stopper is adjacent to said front portion of said plunger rod.

6. The plunger rod assembly of claim 1 wherein said tapered plunger rod wall has a substantially smooth surface.

7. The plunger rod assembly of claim 1 wherein said tapered annular inside wall of said stopper has a concavely shaped surface.

8. The plunger rod assembly of claim 1 wherein said tapered annular inside wall of said stopper has a convexly shaped surface.

9. The plunger rod assembly of claim 1 wherein said thermoplastic material is selected from the group consisting of polyurethane, polyester, polyolefin elastomers, polystyrene-polybutadiene-polystyrene, polyamide and polyamide block amide.

10. A plunger rod assembly for use with a syringe barrel having a substantially cylindrical inside wall and provided with a proximal open end to receive the plunger rod assembly and a distal end adapted to receive and be in fluid communication with fluid delivery means comprising:
   a plunger rod including an elongate shaft portion defining a longitudinal axis, a front portion at the distal end of said shaft portion, a circular forward tapered plunger rod wall intersecting said front portion and tapering outwardly from said intersection along said longitudinal axis, a circular rear tapered plunger rod wall connected to said forward tapered plunger rod wall and tapering inwardly from said connection along said longitudinal axis and terminating at a rear portion of said rear tapered plunger rod wall wherein at least one of said tapered plunger rod walls having a convexly shaped surface; and
   a flexible thermoplastic stopper including an annular side wall circumscribing a stopper longitudinal axis, a continuous front wall intersecting said stopper longitudinal axis and being integral with said side wall, an annular exterior front surface formed near the intersection of said front wall and said side wall, a rear edge at the end opposite said front wall and being integral with said annular side wall, an annular exterior rear surface formed near the intersection of said side wall and said rear edge, said front surface and said rear surface being larger in diameter than the syringe barrel inside wall, a front inside surface of said front wall, a forward tapered annular inside wall intersecting said front inside surface and being tapered outwardly from said intersection along said stopper longitudinal axis, said forward tapered annular inside wall being integral with said side wall, said forward tapered annular inside wall being adjacent to said forward tapered plunger rod wall whereby force applied to said elongate shaft portion along said longitudinal axis in the direction of said stopper creates a force component which is directed substantially outwardly from the interface of said forward tapered plunger rod wall and said forward tapered annular inside wall wherein said annular exterior front surface applies more sealing pressure to the syringe barrel inside wall than the initial pressure existing as a result of said front surface being larger than the syringe barrel inside wall, a rear tapered annular inside wall connected to said forward tapered annular wall and being tapered inwardly from said connection along said stopper longitudinal axis and terminating near said rear edge, said rear tapered annular inside wall being integral with said side wall, said rear tapered annular wall being adjacent to said rear tapered plunger rod wall whereby force applied to said elongate shaft portion along said longitudinal axis in a direction away from said stopper creates a force component which is directed substantially outwardly from the interface of said rear tapered plunger rod wall and said rear tapered annular inside wall wherein said annular exterior rear surface applies more sealing pressure to the syringe barrel inside wall than the initial pressure existing as a result of said rear surface being larger than the syringe barrel inside wall.

11. The plunger rod assembly of claim 10 wherein said front portion of said plunger rod includes a flat surface in a plane substantially perpendicular to said longitudinal axis.

12. The plunger rod assembly of claim 10 wherein said front wall of said stopper is convexly shaped.

13. The plunger rod assembly of claim 10 wherein said front inside surface of said stopper is adjacent to said front portion of said plunger rod.

14. The plunger rod assembly of claim 10 wherein said forward tapered plunger rod wall has a substantially continuous smooth surface.

15. The plunger rod assembly of claim 10 wherein said rear tapered plunger rod wall has a substantially continuous smooth surface.

16. The plunger rod assembly of claim 10 further including an annular rear portion integral with said stopper and projecting proximally from said rear edge of said stopper, said rear portion including a rear annular rib projecting radially outwardly therefrom and being larger in diameter than the inside wall of the syringe barrel.

17. The plunger rod assembly of claim 10, wherein an undercut neck portion is connected to said rear portion of said rear tapered plunger rod wall, said undercut neck portion being smaller in diameter than the smallest diameter of said rear tapered plunger rod wall and being positioned around said longitudinal axis.

18. The plunger rod assembly of claim 17 further including an annular rear portion integral with said stopper and projecting proximally from said rear edge of said stopper, said rear portion including a rear annular rib projecting radially outwardly therefrom and being larger in diameter than the inside wall of the syringe barrel, said rear portion including a flange projecting radially inwardly therefrom adjacent to said rib and adapted to fit into said undercut neck portion to assist in maintaining the positional relationship of said stopper and said plunger rod.

19. The plunger rod assembly of claim 10 wherein at least one of said tapered annular inside walls of said stopper is concavely shaped.

20. The plunger rod assembly of claim 10 wherein at least one of said tapered annular inside walls of said stopper is convexly shaped.

21. The stopper of claim 10 wherein said thermoplastic material is selected from the group consisting of polyurethane, polyester, polyolefin elastomers, polystyrene-polybutadiene-polystyrene, polyamide and polyamide block amide.

22. A syringe assembly comprising:
   a syringe barrel having a substantially cylindrical inside wall and including a proximal open end and a distal end adapted to receive and be in fluid communication with fluid delivery means;
   a plunger rod including an elongate shaft portion defining a longitudinal axis and having a tapered tip portion at the distal end thereof, said tapered tip portion including a front portion at the distal end thereof and a circular tapered plunger rod wall connected to said front portion and having a convexly shaped surface;
   a flexible cup-shaped thermoplastic stopper contained within said syringe barrel, said stopper including an annular side wall, a continuous front wall connected to said side wall, an exterior surface of said annular side wall being larger in diameter than said syringe barrel inside wall, an inside surface of said front wall, a tapered annular inside wall connected to said annular side wall, said tapered annular inside wall and said inside surface being connected and defining a cavity which has said tapered tip portion received therein, said tapered annular inside wall having a substantially continuous smooth surface, said tapered annular inside wall being inclined in the same direction as said tapered plunger rod wall and adjacent thereto whereby force applied to said shaft portion in the direction of descending taper of said tapered plunger rod wall creates a force component which is directed substantially outwardly from the interface of said tapered plunger rod wall and said tapered annular inside wall wherein said exterior surface applies more pressure to said syringe barrel inside wall than the initial pressure existing as a result of said exterior surface being larger than said syringe barrel inside wall; and cooperating means for maintaining the positional relationship of said stopper and said plunger rod.

* * * * *